United States Patent [19]

Kumada et al.

[11] Patent Number: 5,187,444
[45] Date of Patent: Feb. 16, 1993

[54] SENSOR FOR SENSING THE PRESENCE OF ELECTROLYTE SOLUTION

[75] Inventors: Akira Kumada, Kanagawa; Eiichi Takata; Michihiro Murata, both of Kyoto, all of Japan

[73] Assignee: Murata Mfg. Co., Ltd., Kyoto, Japan

[21] Appl. No.: 383,412

[22] Filed: Jul. 20, 1989

[30] Foreign Application Priority Data

Jul. 29, 1988 [JP] Japan .................. 63-190861

[51] Int. Cl.$^5$ ............................ G01R 27/26
[52] U.S. Cl. ......................... 324/663; 324/672
[58] Field of Search ............ 324/664, 663, 665, 667, 324/672, 689, 450; 73/61.1 R, 61 R

[56] References Cited

U.S. PATENT DOCUMENTS

| | | | |
|---|---|---|---|
| 2,709,785 | 5/1955 | Fielden | 324/71.4 |
| 3,096,591 | 7/1963 | Higgins et al. | 324/61 R |
| 3,365,659 | 1/1968 | Breuer | 324/450 |
| 3,774,185 | 11/1973 | Parth | 73/61.1 R |
| 4,240,028 | 12/1980 | Davis, Jr. | 324/61 R |
| 4,426,618 | 1/1984 | Ronchetti et al. | 324/724 |
| 4,600,967 | 7/1986 | Ling et al. | 501/134 |
| 4,673,927 | 6/1987 | Cianciavicchia et al. | 73/61 R |
| 4,751,842 | 6/1988 | Ekrann et al. | 73/61.1 R |

FOREIGN PATENT DOCUMENTS 548798 6/1975 U.S.S.R. .................. 324/61 R

OTHER PUBLICATIONS

Industrial Instruments Inc., Catalog 27, 1963 pp. 18–19.

Primary Examiner—Jack B. Harvey
Assistant Examiner—Maura K. Regan
Attorney, Agent, or Firm—Koda and Androlia

[57] ABSTRACT

A liquid sensor for detecting, in a non-contact manner, whether an electrolyte solution is flowing through a pipeline. A pair of electrodes, on which an AC voltage is impressed, are mounted on the outer surface of a pipeline formed of a material having a high dielectric constant, such as a ceramic, and a discrimination between the presence and the absence of the electrolyte solution in the pipeline is made based on variations in capacitance between the electrodes. In the presence of the electrolyte solution flowing through the pipeline, the capacitance between the electrodes is high because of the conductivity of the electrolyte solution. In the absence of the electrolyte solution flowing through the pipeline, the capacitance is determined by air and is, therefore, low. Since the electrodes are maintained in a non-contact relation with the electrolyte solution, degradation of characteristics due to corrosion is obviated. The absence of intermediates which, if present, would cause a lowering in detection sensitivity ensures an extremely high accuracy of detection.

4 Claims, 6 Drawing Sheets

SENSOR FOR SENSING THE PRESENCE OF ELECTROLYTE SOLUTION

BACKGROUND OF THE INVENTION

1. Field of the Invention

This invention relates to a liquid sensor, and more particularly to a liquid sensor for non-contact discrimination between the presence and the absence of an electrolyte solution flowing through a pipeline or tube.

2. Description of the Prior Art

There have been known liquid sensors for checking whether water containing an electrolyte dissolved therein is flowing through a pipeline or not.

FIG. 6 shows an example of a conductivity sensor for detecting the presence or absence of an electrolyte solution flowing through a pipeline, according to the prior art. In the figure, the pipeline 2 through which the electrolyte solution 1 flows intermittently is provided with a pair of electrodes 3a and 3b disposed at a predetermined interval to penetrate into the pipeline 2, and a predetermined voltage is impressed on the electrodes from a power supply, not shown, through respective lead wires 4a and 4b.

As is well known, an aqueous solution containing an electrolyte shows an extremely high electric conductivity, whereas air has an extremely low conductivity.

When the electrolyte solution flows through the pipeline 1, therefore, the electric resistance between the electrodes 3a and 3b is lowered, and by detection of the lowering it is possible to find the presence of the electrolytic solution in the pipeline 1.

When the electrolyte solution is not flowing through the pipeline 1, on the other hand, the conductivity between the electrodes 3a and 3b is low because of the presence of air, and the electric resistance between the electrodes is extremely high, as compared with that in the presence of the electrolyte solution flowing through the pipeline 1.

Accordingly, it is possible to check whether the electrolyte solution is present or absent in the pipeline 2, based on variations in the electric resistance between the electrodes 3a and 3b.

As a contrast to the above conductivity sensors of the type in which electrodes make direct contact with an electrolyte solution, there have been known non-contact type optical liquid sensors, one example of which is illustrated in FIG. 7.

The non-contact type sensor, also intended for discrimination between the presence and the absence of the liquid flowing through the pipeline 2, comprises a light emitting diode (LED) 5 and a phototransistor 6 disposed opposite to each other on the wall surface of the pipeline 2. Light is transferred between the LED 5 and the phototransistor 6, and the presence of the electrolyte flowing through the pipeline 2 is distinguished based on the difference between the photoelectric output in the presence of the solution and the photoelectric output in the absence of the solution.

Namely, in the absence of the solution in the pipeline 2, the light emitted from the LED 5 is received, substantially as it is, by the phototransistor 6, which generates an extremely high photoelectric output. In the presence of the electrolyte solution flowing through the pipeline 2, on the other hand, the light from the LED 5 is attenuated by the solution itself and by the turbidity, color or the like, so that the photoelectric output of the phototransistor 6 is extremely low, as compared with the output in the absence of the solution in the pipeline. Thus, it is possible to detect whether the solution is flowing through the pipeline 2 or not.

However, the contact-type liquid sensor as shown in FIG. 6 involves the direct contact of the electrolyte solution with the electrodes 3 and, therefore, there is the possibility that various chemical substances contained in the solution 1 may deposite on the electrodes 3 or the electrodes 3 themselves may be dissolved, resulting in marked deterioration of the performance of the sensor.

In view of the above, plating the electrodes 3 with copper, silver or other precious metal may be contemplated. The plating, however, leads to a large increase in the cost of the sensor.

There may arise a further problem, particularly where the electrolyte solution 1 intermittently flows and stops flowing, repeatedly, at relatively short intervals of time. Namely, a detection result similar to that obtained in the presence of the solution 1 flowing through the pipeline may be produced in the absence of the solution, due to the drops of the solution remaining in the pipeline 2. For obviating such a situation, it is necessary to provide a wide spacing between the electrodes, which causes a lowering in the sensitivity of detection and a limitantion on the control range.

On the other hand, the optical type sensor illustrated in FIG. 7, which is capable of non-contact detection, has the problem that the pipeline 2 must be formed of a transparent material for permitting the transmission of light through the walls of the pipeline. Besides, the attenuation of the light transmitted through the solution constitutes the condition for discrimination between the presence and the absence of the solution. Therefore, where the solution is a colorless transparent solution, the attenuation coefficient is extremely low and, accordingly, there is a possibility of such a malfunction that the solution actually flowing through the pipeline may be judged absent.

SUMMARY OF THE INVENTION

It is accordingly an object of this invention to provide a liquid sensor which overcomes the above-mentioned difficulties or inconveniences, has a simple and inexpensive construction, with protection of electrodes, and has excellent detection accuracy.

To attain the above-mentioned object, this invention provides a liquid sensor comprising a pipeline which is formed by use of a dielectric having a dielectric constant of at least 100 and through which an aqueous solution containing an electrolyte flows, and at least one pair of electrodes oppositely disposed along the outer surface of the pipeline and maintained in a non-contact relation with the aqueous solution, whereby a discrimination between the presence and the absence of the aqueous solution in the pipeline is made based on variations in capacitance detected by impressing an AC voltage between the electrodes.

According to the invention as above, the material constituting the pipeline through which an electrolyte solution flows has an extremely high dielectric constant. Therefore, though the electrodes are mounted on the outer surface of the pipeline in a non-contact relation with the electrolyte solution, the increase in AC impedance due to the presence of the pipeline between the electrodes is substantially negligible.

Besides, the electrodes function as a capacitor when an AC voltage is impressed between them, so that it is possible to discriminate between the presence and the absence of the electrolyte solution in the pipeline, based on variations in the capacitance between the electrodes.

As mentioned above, the electrodes are maintained in a non-contact relation with the electrolyte solution and, therefore, it is possible to prevent the deterioration of the characteristics of the electrodes due to corrosion or the like. Moreover, the absence of intermediates which would, if present, cause a lowering in the detection sensitivity ensures an extremely high accuracy of detection.

BRIEF DESCRIPTION OF THE DRAWSINGS

DESCRIPTION OF THE PREFERRED EMBODIMENTS

Figure 1A:
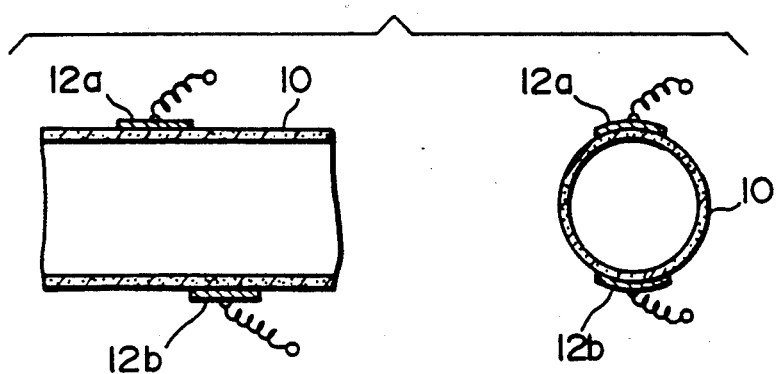
FIG. 1 is a schematic illustration of a liquid sensor according to this invention.

The preferred embodiments of this invention will now be described below while referring to the drawings.

FIG. 1 shows an exemplary scheme of a liquid sensor according to this invention.

What is intended by the invention is to secure an excellent detection accuracy while protecting electrodes from bad chemical effects of an electrolyte solution, which is the object to be detected. To maximize the sensitivity of the electrodes for detecting the electrolyte solution, it is naturally desirable to maintain the electrodes and the solution in direct contact. As has been mentioned above, however, such an arrangement is inevitably attended by adverse secondary effects such as corrosion of the electrodes under the action of the electrolyte solution.

On the other hand, an arrangement aimed primarily at the protection of the electrodes necessitates a protective measure, such as coating the detecting surfaces of the electrodes with some material. In that case, the presence of a coating material between the electrode and the electrolyte solution leads inevitably to a lowering in the detection sensitivity.

In search of means for fulfilling both of the above-mentioned contradictory conditions, this invention has been accomplished based on an idea that it is a key to the solution of the above-mentioned problems to develop a material which, when disposed intermediately between each electrode and an electrolyte solution, does not increase the impedance between the electrodes by the intrinsic properties thereof. Dielectric constant has been adopted as an index of the suitability of materials for use as the desired material.

In this embodiment, ceramics were concluded to be best suited for use as a material having a dielectric constant of at least 100 and being most favorably applicable to the liquid sensor from the viewpoints of corrosion resistance, physical durability, cost, etc. With the ceramic material disposed intermediately between each electrode and the electrolyte solution, an arrangement has been realized which is capable of effective protection of the electrodes from the chemical actions of the electrolyte solution, without significant lowering in the sensitivity for detection of the electrolyte solution.

In FIG. 1(A), the pipeline 10 through which the electrolyte solution flows is, per se, formed by use of a ceramic dielectric having an extremely high dielectric constant. The ceramic material may be any of the ceramics having a composition and a dielectric constant r set forth below. Other than the exemplary ceramics, the so-called high dielectric constant ceramics may also be used.

| Composition | $\epsilon r$ (at 25° C.) |
| --- | --- |
| $BaTiO_3$ | 1,500 |
| $(BaO.8SrO.2)TiO_3$ | 6,000 |
| $(PbO.3SrO.7)TiO_3$ | 1,000 |
| $(BaO.98MgO.02)TiO_3$ | 1,500 |

As is clear from the figure, a pair of electrodes 12a and 12b in this embodiment are charcterized in that they are mounted on the outer surface of the ceramic pipe.

According to the invention, therefore, the electrodes 12a and 12b are placed in an utter non-contact relation with the electrolyte solution flowing through the ceramic pipe 10, so that it is possible to securely prevent the characteristics of the electrodes from being deteriorated by the chemical actions of the electrolyte solution. Discrimination between the presence and the absence of the electrolyte solution flowing through the ceramic pipeline 10 is made on the basis of variations in the capacitance between the electrodes 12a and 12b detected by impressing a predetermined AC voltage between the electrodes in the presence and in the absence of the electrolyte solution. Since the ceramic pipeline 10 present between the electrodes has an extremely high dielectric constant as mentioned above, the intrinsic capacitance of the ceramic pipeline 10 itself is extremely high.

In the absence of the aqueous solution in the pipeline 10, on the other hand, the capacitance between the electrodes is determined by air present in the pipeline 10 and, therefore, is extremely low.

Consequently, according to the invention, when the aqueous solution is flowing through the pipeline 10, the capacitance between the electrodes takes a high value detemined by the high dielectric constant of the ceramic pipeline 10, because the aqueous solution is highly conductive. When the aqueous solution is not flowing through the pipeline 10, the capacitance between the electrodes is extremely low because it is determined by the air present in the pipeline 10, as mentioned above. As a consequence of the above, it is possible to make easy discrimination between the presence and the absence of the aqueous solution in the pipeline 10 according to the invention.

Figure 1B:
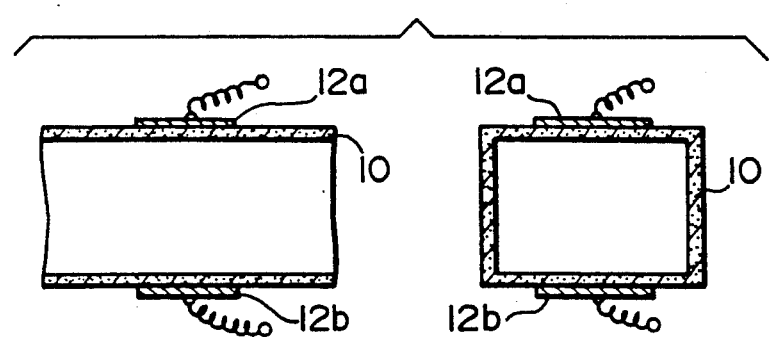

FIG. 1(B) shows an exemplary scheme in which the pipeline has a tubular form with a tetragonal cross-sectional shape and the principle of which is the same as in FIG. 1(A).

Figure 2A:
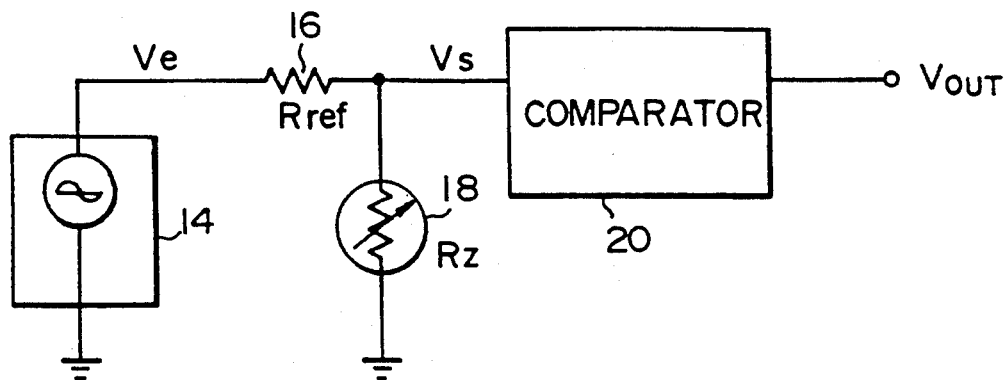
FIG. 2 is a schematic circuit diagram of the liquid sensor according to the invention.

FIG. 2(A) is a schematic total circuit diagram of the liquid sensor according to this invention.

An AC voltage Ve supplied from an oscillating circuit 14 is impressed, through a reference resistor Rref 16, on the electrodes 12a and 12b of a sensor portion 18 comprising a variable resistance Rz of which one output terminal is earthed.

A voltage Vs, outputted from the sensor portion 18, corresponding to variations in the impedance between the electrodes 12a and 12b is supplied as a detection signal to a comparing circuit portion 20, in which the detection signal is compared with a predetermined reference voltage. A signal of voltage Vout indicative of the presence or absence of the electrolyte solution in the ceramic pipeline 10, based on the result of the comparison, is outputted toward a display device or the like, not shown.

While the description has been made hereinabove of the circuit scheme comprising basic elements for discrimination between the presence and the absence of the electrolyte solution in the ceramic pipeline 10, specific operations of the circuit will now be explained below while referring to FIGS. 3 and 4.

Figure 3:
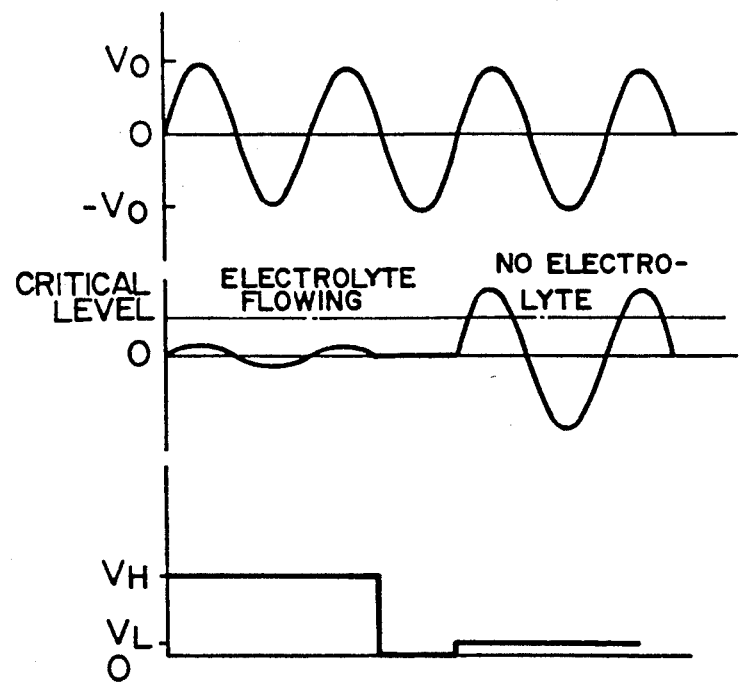
FIG. 3 is a timing chart illustrating the operation of the liquid sensor according to this invention.
Figure 2B:
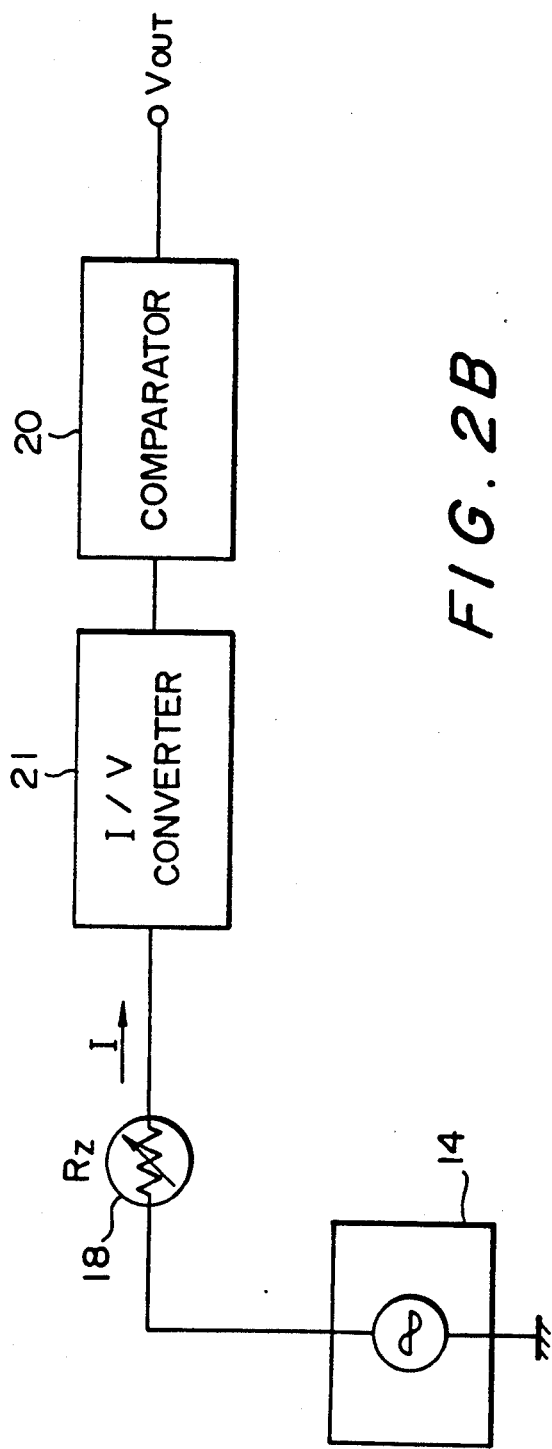

FIG. 3 is a timing chart showing the voltage levels of the signals outputted respectively from the oscillating circuit 14, the sensor portion 18 and the comparing circuit 20 in the arrangement shown in FIG. 2. The oscillating circuit 14 continuously outputs AC voltage signal represented by a sine wave, as shown, at a predetermined period.

The voltage signal from the oscillating circuit 14 is applied to the electrode plates 12a and 12b of the sensor portion 18 via the reference resistor Rref 16.

The electrode plates 12a and 12b constitute a capacitor with the ceramic pipeline 10 therebetween, and the capacitance between the electrode plates is represented as varied according to whether the intermediate substance in the pipeline 10 is air or the electrolyte solution, namely, according to the absence or the presence of the electrolyte solution flowing through the ceramic pipeline 10.

FIG. 4 shows equivalent circuits for the sensor portion according to this invention, sandwiched between the electrode plates 12a and 12b and regarded as a capacitor, in the absence and in the presence of the electrolyte solution flowing through the ceramic pipeline 10.

Figure 4A:
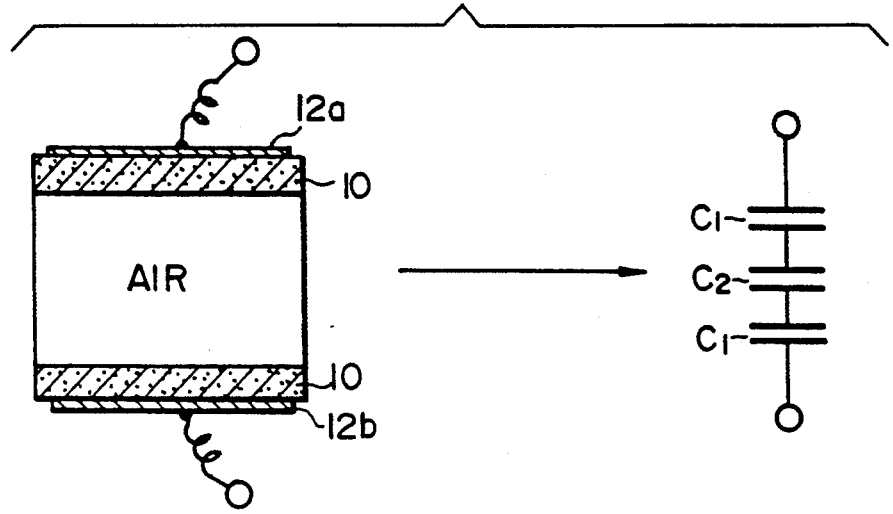
FIG. 4 shows equivalent circuit diagrams for the system between electrodes in the liquid sensor, in the presence and in the absence of an electrolyte solution flowing through a pipeline.

FIG. 4(A) shows the equivalent circuit for the sensor portion in the absence of the electrolyte solution flowing. Let the capacitances of the ceramic pipeline 10, air, and the ceramic pipeline 10 located between the electrode plates 12a and 12b be C, C and C respectively, then the series combined capacitance C thereof is obtained from the following formula:

$$1/C = 1/C_1 + 1/C_2 + 1/C_1$$
$$= (2C_2 + C_1)/C_1C_2$$
$$C = C_1C_2/2C_2 + C_1$$

Thus, it is understood that the capacity between the electrode plates 12a and 12b in the absence of the electrolyte solution flowing is extremely low.

Figure 4B:
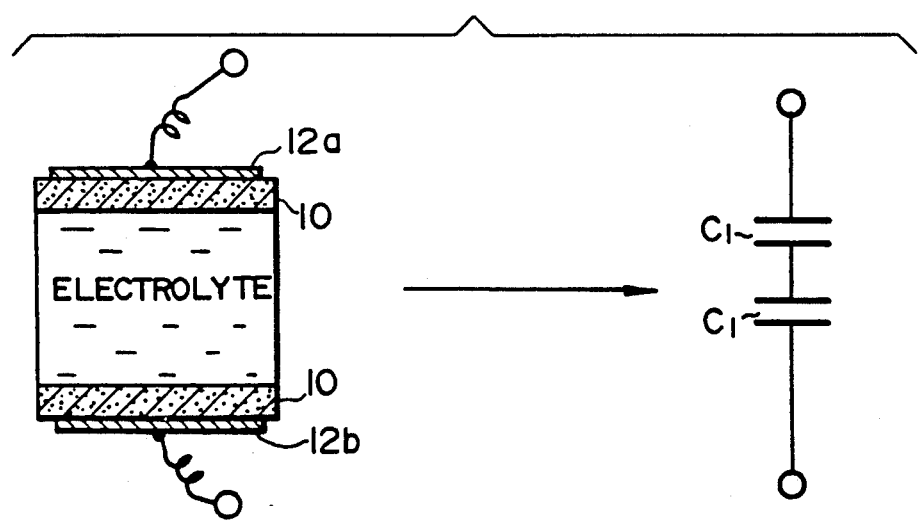

On the other hand, when the electrolyte solution is flowing through the ceramic pipeline 10, as shown in FIG. 4(B), the conductivity of the electrolyte solution itself is extremely high due to the electrolytic dissociation, as is well known. Therefore, it is possible to deem the inner walls of the pipeline 10 electrically connected to each other by the electrolyte solution when low frequency-AC signals are detected by the sensor portion 18. In addition, the ceramic pipeline 10 has a high dielectric constant, as mentioned above, and the series combined capacitance C is therefore, very high. Accordingly, the capacitance between the electrode plates 12a and 12b is given as follows:

$$1/C_1 = 1/C + 1/C_1$$
$$= 1/C_1$$

$$C = C_1/2$$

From the foregoing it is understood that the capacity between the electrode plates 12a and 12b in the presence of the electrolyte solution flowing through the ceramic pipeline is extremely high.

Referring back to FIG. 3, the output voltage from the sensor portion 18 shows variations in voltage waveform as represented by the solid lines in the figure, according to the presence and absence of the electrolyte solution flowing through the pipeline. The waveforms are compared by the comparing circuit 20 with a critical level of voltage preset in the circuit 20.

The critical voltage level is set at a predetermined value, with the reference voltage Ve from the oscillating circuit 14 taken as 0 (zero). As is clear from the figure, the output voltage from the sensor portion in the presence of the electrolyte solution flowing through the pipeline 10 converges to the vicinity of the reference voltage, and does not reach the critical voltage level.

On the other hand, when the electrolyte solution is absent from the interior of the ceramic pipeline and the intermediate between the electrode plates is air, the output voltage from the sensor portion 18 shows an extremely great amplitude, as shown, and periodically exceeds the critical voltage level.

The comparing circuit 20 compares the output voltage from the sensor portion 18 with the reference voltage, and when the detected voltage is not more than the reference votlage, the circuit 20 outputs a high-level signal, whereas when the detected voltage exceeds the reference voltage, the circuit 20 generates a low-level output signal.

Thus, when the electrolyte solution is flowing through the ceramic pipeline 10, the comparing circuit 20 output a high-level signal, which is supplied to a display device, not shown, thereby enabling the use to recognize securely the condition in the pipeline 10.

It is naturally possible to contrive a further higher performance by disposing a control circuit or an amplifying circuit ahead of the comparing circuit 20.

As shown in FIG. 2(A), it is also possible to connect the oscillating circuit 14, the sensor portion 18 and a current-voltage convertor 21 in series with each other, thereby forming a detection circuit which operates based on the magnitude of the AC current flowing according to the variations in the impedance of the sensor portion 18.

As has been described above, according to the liquid sensor of this invention, in which a ceramic having a high dielectric constant is used as a material for the pipeline through which an electrolyte solution flows, the capacitance between the electrode plates attached to the outer surface of the ceramic pipeline varies greately depending on whether the substance present in the pipeline 10 is the electrolyte solution or air. Namely, the capacitance between the electrode plates 12a and 12b varies depending only on the presence or absence of the electrolyte solution flowing through the pipeline.

Therefore, it is possible to grasp the condition in the ceramic pipeline 10 easily, accurrately and assuredly, based on the variations in the capacitance.

Since the electrode plates 12a and 12b are fitted to the outer surface of the pipeline 10, the electrodes do not suffer the chemical actions of the electrolyte. Besides, since the material constituting the pipeline is a ceramic having characterized by a high dielectric constant, mouting the electrode plates on the outer surface of the pipeline does not lead to a lowering in the detection sensitivity due to the presence of the pipeline between the electrode plates.

Furthermore, even when the electrolyte solution is left on the wall surface of the ceramic pipeline 10 immediately after the solution steps flowing through the pipeline 10, the effect of the remaining solution on the capacity between the electrode plates 12a and 12b is almost negligibly small and, therefore, does not cause such malfunctions as occur in the prior-art systems.

Though the sensor portion 18 in the embodiment comprises two flat platelike electrodes, the electrodes may be so formed as to surround entirely the outer surface of the tubular ceramic pipeline.

Figure 1C:
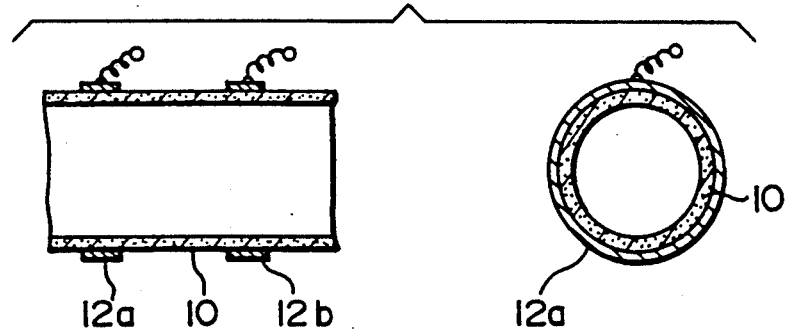

Moreover, as shown in FIG. 1(C), a pair of electrodes may be provided in the form of an annular belt along the entire outer circumference of the tubular ceramic pipeline.

Figure 5A:
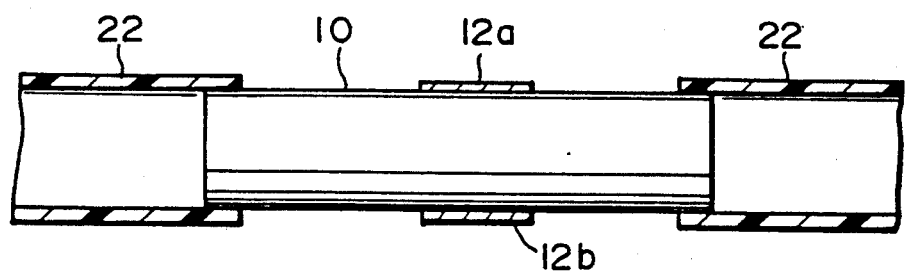
FIG. 5 is a schematic illustration of a second embodiment of this invention.
Figure 5B:
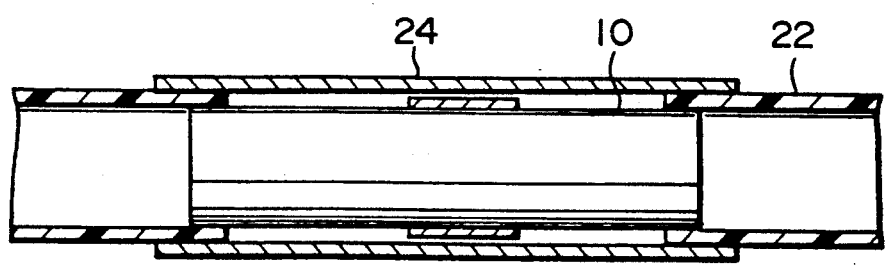
Figure 6:
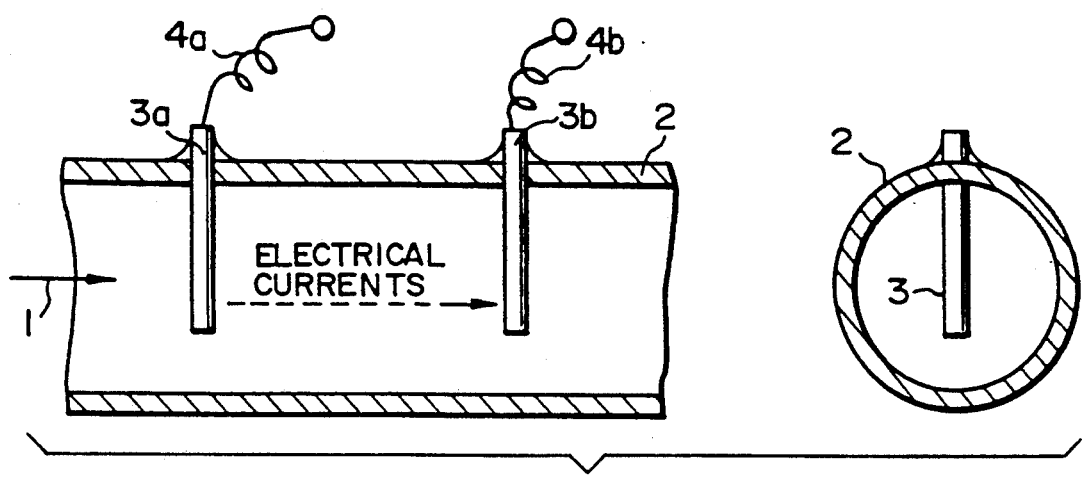
FIGS. 6 and 7 are each a schematic illustration of a liquid sensor according to the prior art.
Figure 7:
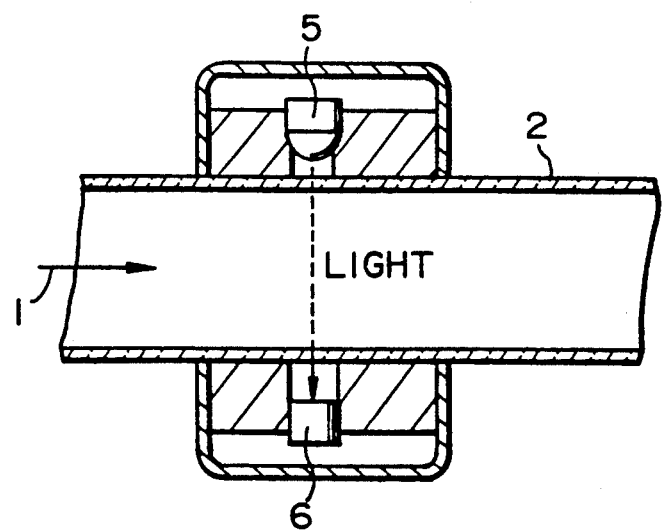

FIG. 5 shows a second embodiment of the liquid sensor according to this invention.

This embodiment is characterized in that the pipeline through which the electrolyte solution flows is not entirely formed of a ceramic but is formed of the ceramic only in the vicinity of the portions on which to mount the electrodes. Though a little complicated structurally, this arrangement enables minimization of the amount of ceramic pipeline used, and therefore contributes greatly to the reduction of the manufacturing cost.

Namely, as shown in FIG. 5(A), the ceramic pipeline 10 on which the electrodes 12a and 12b are mounted is inserted in a portion of the pipeline 22 through which the electrolyte solution flows, and the pipelines 22 and 10 are covered by a polyvinyl chloride tube 24. The pipeline 22 is preferably constituted of a silicone tube or the like.

According to the second embodiment, it is possible to restrict the use the ceramic pipeline 10 to only the required portion and use a more inexpensive material, such as silicone tube, for the other portions of the object to be detected, while maintaining substantially the same detection function and effects as in the first embodiment. It is therefore possible to achieve a great reduction in cost and to impart flexibility to the sensor device.

Thus, according to the invention, a ceramic characterized by an extremely high dielectric constant is used for the entire part or a part of the pipeline through which an electrolyte solution flows, and electrodes for constituting the capacitor are attached to the outer surface of the ceramic, thereby protecting the electrodes from the chemical actions of the electrolyte solution. Consequently, it is possible to remove completely the disadvantage of the electrodes being immersed in the electrolyte solution, and to maintain an extremely high sensitivity for detection of the electrolyte solution due to the high dielectric constant property of the ceramic.

As has been described above, according to this invention, a material having a high dielectric constant is used as a material for a pipeline through which an electrolyte solution flows, so that it is possible to realize high-accuracy detection of the electrolyte solution while maintaining the electrodes in a non-contact relation with the electrolyte solution.

What is claimed is:

1. A liquid sensor comprising:
    a partially-cutout pipeline through which an aqueous solution containing an electrolyte flows;
    a ceramic pipe formed by use of a dielectric having a dielectric constant of at least 100 and inserted into a partial cutout portion of said partially-cutout pipeline such that both end portions thereof are connected to the pipeline;
    at least one pair of electrodes disposed on the outer surface of said pipeline;
    an oscillating circuit for supplying an AC voltage at a predetermined level on said pair of electrodes; and
    a plastic sleeve for covering joint portions of said pipeline and said ceramic pipe;
    whereby a discrimination between the presence and the absence of the aqueous solution in said pipeline is made based on variation in capacitance detected by impressing an AC voltage between said electrodes.

2. A liquid sensor as set forth in claim 1, wherein said pair of electrodes are each provided in the form of an annular belt surrounding the outer surface of said ceramic pipe, and are disposed at a predetermined interval along the longitudinal direction of said pipe.

3. A liquid sensor as set forth in claim 1, wherein said sensor further comprises:
    a comparing circuit for comparison of an output signal from the electrodes having a voltage corresponding to an impedance change between the electrodes upon impressing of the AC voltage with a preset critical voltage.

4. The liquid sensor as set forth in claim 1, wherein the pipeline comprises a plastic tube having a flexibility.

* * * * *